(12) United States Patent
Freedman

(10) Patent No.: US 6,454,761 B1
(45) Date of Patent: Sep. 24, 2002

(54) LASER SURGERY DEVICE AND METHOD

(76) Inventor: Philip D. Freedman, 6000 Wescott Hills Way, Alexandria, VA (US) 22315-4747

(*) Notice: Subject to any disclaimer, the term of this patent is extended or adjusted under 35 U.S.C. 154(b) by 0 days.

(21) Appl. No.: 08/380,639

(22) Filed: Jan. 30, 1995

(51) Int. Cl.[7] .................................................. A61B 18/18
(52) U.S. Cl. ................................ 606/5; 606/3; 606/10; 606/12; 606/13; 600/407; 600/425; 600/473; 600/476
(58) Field of Search ..................... 606/2, 3–7, 10–17; 600/407, 425, 473, 476

(56) References Cited

U.S. PATENT DOCUMENTS

| | | | |
|---|---|---|---|
| 4,126,136 A | | 11/1978 | Auth et al. |
| 4,240,431 A | | 12/1980 | Komiya |
| 4,316,467 A | | 2/1982 | Muckerheide |
| 4,476,512 A | | 10/1984 | Sunago et al. |
| 4,564,012 A | | 1/1986 | Shimada et al. |
| 4,580,557 A | | 4/1986 | Hertzmann |
| 4,648,400 A | | 3/1987 | Schneider et al. |
| 4,669,466 A | * | 6/1987 | L'Esperance ................... 606/5 |
| 4,672,963 A | | 6/1987 | Barken |
| 4,692,924 A | | 9/1987 | Koisumi et al. |
| 4,838,679 A | * | 6/1989 | Bille ........................... 351/221 |
| 4,950,267 A | | 8/1990 | Ishihara et al. |
| 4,994,059 A | | 2/1991 | Kosa et al. |
| 4,995,716 A | * | 2/1991 | Warnicki et al. ............. 351/221 |
| 5,035,693 A | | 7/1991 | Kratzer et al. |
| 5,054,924 A | * | 10/1991 | Hochberg .................... 356/359 |
| 5,071,251 A | * | 12/1991 | Hochberg et al. ............ 356/359 |
| 5,123,902 A | | 6/1992 | Muller et al. |
| 5,148,807 A | * | 9/1992 | Hsu ............................. 128/645 |
| 5,154,707 A | | 10/1992 | Rink et al. |
| 5,159,361 A | * | 10/1992 | Cambier et al. ............. 351/212 |
| 5,188,633 A | | 2/1993 | Kratser et al. |
| 5,200,604 A | | 4/1993 | Rudko et al. |
| 5,221,142 A | | 6/1993 | Snow |
| 5,227,861 A | | 7/1993 | Nishizawa et al. |
| 5,231,285 A | | 7/1993 | Berg |
| 5,262,636 A | | 11/1993 | Rink |
| 5,284,477 A | | 2/1994 | Hanna et al. |
| 5,285,260 A | | 2/1994 | Dumoulin |
| 5,301,003 A | | 4/1994 | Ikeda |
| 5,303,030 A | | 4/1994 | Abraham et al. |
| 5,317,389 A | * | 5/1994 | Hochberg et al. ............ 351/211 |
| 5,318,047 A | * | 6/1994 | Davenport et al. ............. 606/5 |
| 5,323,229 A | | 6/1994 | May et al. |
| 5,329,356 A | | 7/1994 | Tabarelli et al. |
| 5,334,191 A | | 8/1994 | Poppas et al. |
| 5,337,144 A | | 8/1994 | Strul et al. |
| 5,341,211 A | | 8/1994 | Prinzhausen et al. |
| 5,342,351 A | | 8/1994 | Blaha et al. |
| 5,346,488 A | | 9/1994 | Prince et al. |
| 5,347,326 A | | 9/1994 | Volk |
| 5,349,440 A | | 9/1994 | DeGroot |
| 5,350,376 A | | 9/1994 | Brown |
| 5,354,323 A | | 10/1994 | Whitebook |
| 5,355,209 A | | 10/1994 | Grosso |
| 5,355,217 A | | 10/1994 | Canteloup et al. |
| 5,359,173 A | * | 10/1994 | Opdyke .................. 219/121.69 |
| 5,361,131 A | | 11/1994 | Tekemori et al. |
| 5,365,340 A | | 11/1994 | Ledger |
| 5,387,951 A | * | 2/1995 | Hatakana ..................... 351/221 |
| 5,395,356 A | | 3/1995 | King et al. |
| 5,406,342 A | * | 4/1995 | Jongsma ..................... 351/221 |
| 5,459,570 A | * | 10/1995 | Swanson et al. ............. 356/479 |

OTHER PUBLICATIONS

Hariharan, Interferometers Chapter 21, *Handbook of Optics*, McGraw–Hill (1995), pp. 21.2–21.28.

Berns, Laser Surgery, *Scientific American*, (1991), pp. 84–90.

MIT Reporter, *Technology Review*, (1994), pp. 10–11.

* cited by examiner

*Primary Examiner*—David M. Shay
(74) *Attorney, Agent, or Firm*—Philip D. Freedman

(57) ABSTRACT

Laser surgery is controlled by interferometry.

25 Claims, 2 Drawing Sheets

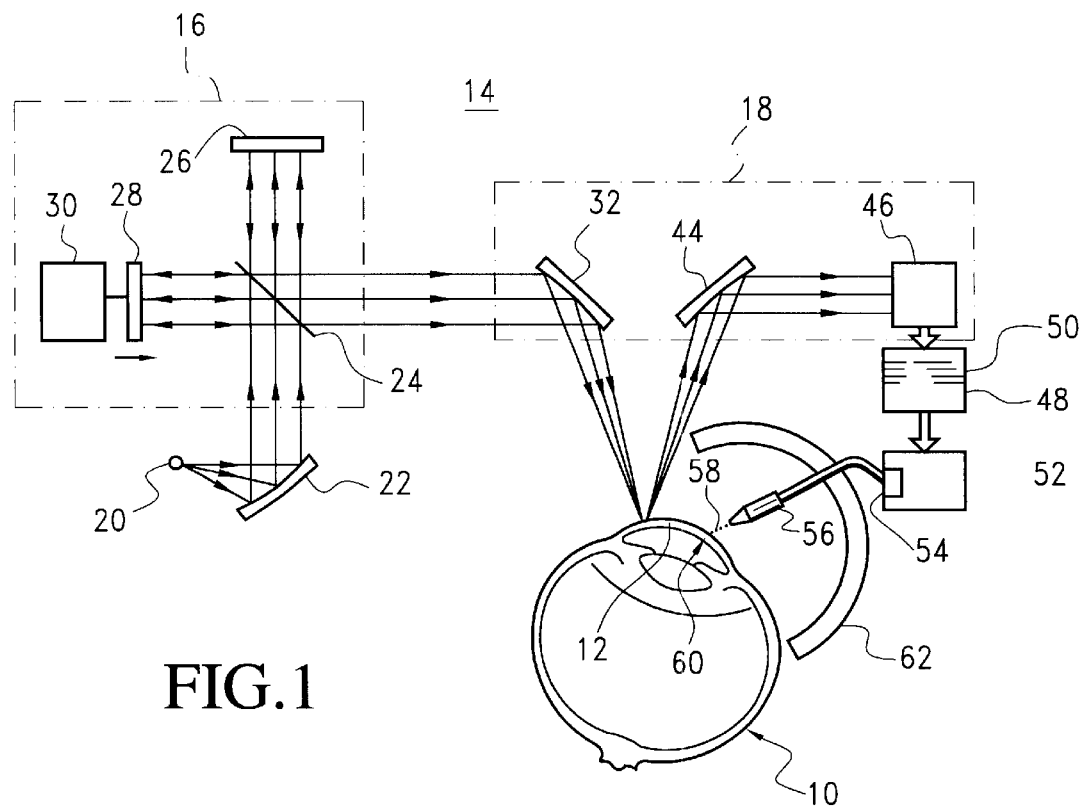
FIG.1
FIG.2
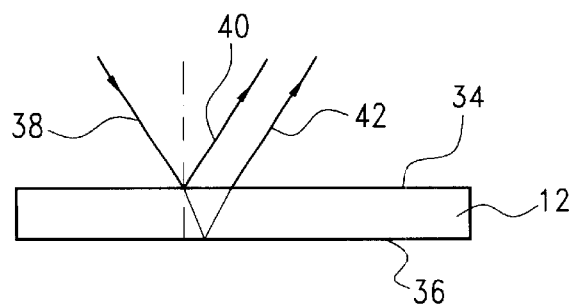

LASER SURGERY DEVICE AND METHOD

BACKGROUND OF THE INVENTION

This invention is directed to a laser surgery device and method controlled by interferometry.

BACKGROUND

Laser surgery methods include ophthalmic procedures, dental procedures and irradiation of tissue for hemostasis, photodynamic destruction of forms of tumors, removal of epidermal growths and abnormalities and for the ablation of atherosclerotic plaques. Lasers have been used in surgical procedures to cut tissue and to immediately coagulate the cut. Lasers have been used to control bleeding during surgical removal of burn wound eschar and in surgery on highly vascularized organs such as the liver.

Typically in laser surgery, heat generated by the laser is harnessed to destroy tissue. While thermal effects are commonly used in medical surgical methods, other nonthermal effects are utilized as well. Photons from laser beams can drive chemical reactions, break atomic bonds that hold molecules together or create shock waves to achieve various surgical objectives. Biomedical applications include such tasks as unclogging obstructed arteries, breaking up kidney stones, clearing cataracts and altering genetic material.

Most laser surgical methods utilize the laser heat effect. If the wavelength of light from the laser is matched very closely with the absorption band of the target structure, the laser light will be absorbed by, and therefore damage only that structure. The heat effect of the laser can be extremely selective and precisely controlled. However, in many surgical methods, it is difficult or impossible to choose an irradiating wavelength that will damage target tissue without affecting surrounding tissue. The absorption wavelength of target tissue may not be known or cannot be determined because of turbidity of tissue or other reasons. The absorption band of target tissue may not be distinguishable from the absorption wavelength of surrounding tissue.

U.S. Pat. No. 4,672,963 to Barken, proposes an automated and integrated system for laser surgery. The position of a laser light guide transmitting laser radiation to selected internal structures is controlled by monitoring through the use of an ultrasonic probe. The ultrasonic probe is coupled to a computer system for providing a multiplicity of cross-section images of the internal body structure. By varying the position of the ultrasonic probe along a known longitudinal dimension, a three-dimension image of the structure is reconstructed from two-dimensional images. The images are interpreted by a computer system or by a computer system in conjunction with a physician to control the parameters of a surgical procedure.

However, the use of ultrasonics to control laser surgery is limited. An ultrasonics procedure requires separate insertion of an ultrasonic probe. For example in the surgical procedure for removal of a prostate gland, an ultrasonic probe is entered in the patient transrectally and a laser probe is entered in the patient intraurethrally. Another problem is that ultrasonics cannot be utilized to construct images of very small structures or smaller elements of larger structures and cannot be utilized to detect certain tissue mass that is located within turbid tissue or within tissue having like sonic characteristics to the target tissue.

SUMMARY OF THE INVENTION

The present invention relates to a method of laser surgery that permits detection and distinguishing of structures 10 microns in size and smaller. The method permits control of laser surgery without requiring an intrusive probe. The method permits detection of tissue mass that is located within turbid tissue or within tissue having sonic characteristics that are identical to the characteristics of target tissue mass.

The invention provides a method and device for laser surgery wherein a treatment laser beam is controlled by interferometry, preferably by optical coherence tomography. The method comprises detecting a surface or mass of biological tissue by a process of interferometry and controlling the laser treating of the biological tissue according to the detected surface or mass.

The device comprises a laser beam irradiator for applying a laser beam to a target region of biological tissue and an interferometer for projecting a light beam onto the target region. The interferometer includes a detector for receiving a reflected interference beam from the target region, detecting a phase difference of the interference beam and providing an electrical signal according to the phase difference. The device includes a controller responsive to the electrical signal for controlling an output of applied laser beam from the laser beam irradiator.

The method can comprise projecting an interference light beam onto a multilayer target of biological tissue, detecting the interference light beam reflected by the multilayer target to provide an interferogram, evaluating the multilayer target on the basis of the interferogram, and controlling the laser treating of the biological tissue according to the evaluating step.

In another embodiment, the method comprises projecting a phase modulated measurement beam onto a target of biological tissue and projecting a reference beam onto a reference target, combining a reflected reference beam reflected from the reference target with a reflected measurement beam reflected by the target of biological tissue, evaluating a phase difference between the reflected reference beam and the reflected measurement beam and controlling the laser treating of the biological tissue according to the evaluating step.

BRIEF DESCRIPTION OF THE DRAWINGS

FIG. 1 and FIG. 3 are schematic representations of devices and methods for laser surgery controlled by low-coherence interferometry.

FIG. 2, FIG. 4 and FIG. 5 are schematic representations of thin film layers of biological tissue such as thin film layers of a cornea.

DESCRIPTION OF PREFERRED EMBODIMENTS

Figure 3:
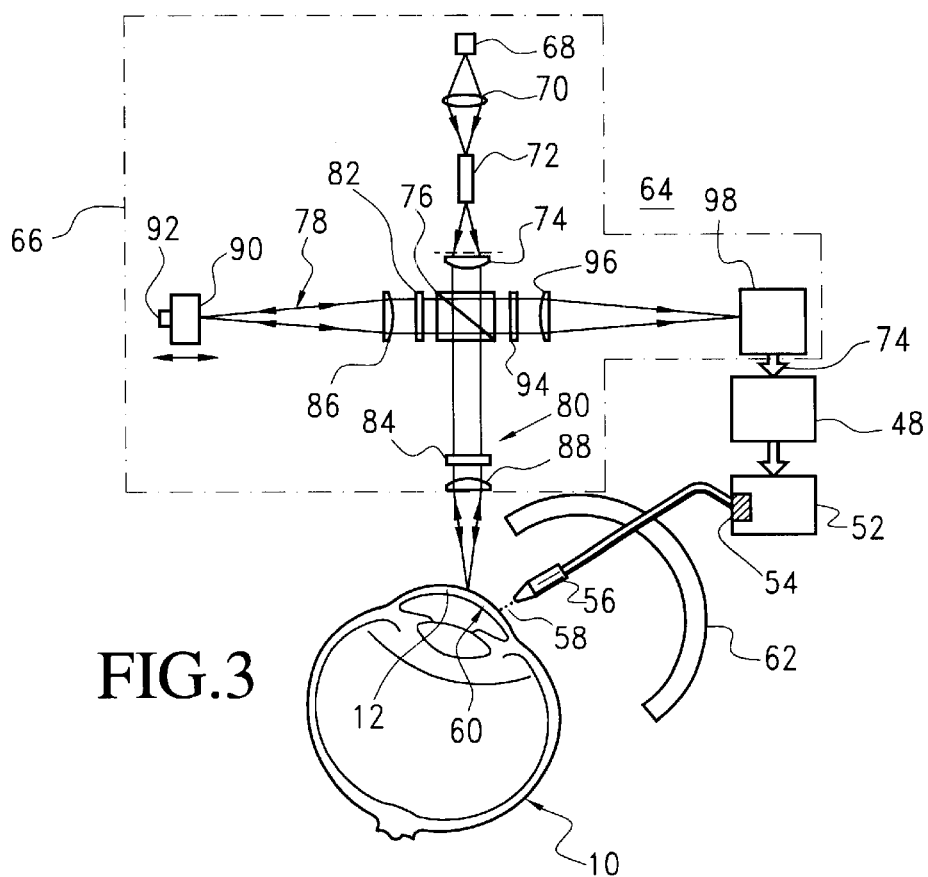

Interferometric measurements require an optical arrangement in which two or more beams, derived from the same source but traveling along separate paths, are made to interfere. Interferometers are classified as two-beam interferometers and multiple-beam interferometers according to the number of interfering beams. Hariharan, Interferometers, Chapter 21, *Handbook of Optics*, McGraw-Hill (1995), provides examples of a number of types of interferometers. The disclosure of this treatise is incorporated herein by reference.

In interferometry, a source generates two identical beams of low-coherence light consisting of many frequencies. Optical coherence tomography utilizes principles of interferometry to provide images of structures 10 microns in size and smaller. In a first method, an optical system synthesizes two light beams in a predetermined wave number region while continuously varying optical path differences to produce an interference light beam. The beam is projected onto a mutilayer thin film sample as a parallel beam having a predetermined beam diameter. An interference light beam reflected by the sample is detected to provide an interferogram.

In another method, one beam is directed to an object (target region) to be examined and a second beam is directed to a reference object. The beams strike the target region and the reference object and return to the source where they combine. If the target region is at the exact distance from the source as the reference object, then a resulting combined beam consists of augmented wavelengths and is a bright, undiminished beam. If the region and the reference object are at different distances, the reflected beams arrive out of sync and brightness of the combined beam is diminished. The distance of the target region can be determined by moving the reference object until the resulting combined beam is brightest.

According to the second method, low-coherence light is split into two identical beams. The first beam is focused at a target region of biological tissue and the second beam at a reference mirror. The tissue and the mirror reflect the separate beams back to a photosensor and the photosensor measures the brightness of a resulting combined beam. Pairs of beams are emitted toward the tissue and mirror while the reference mirror is held steady and the focus of the first beam is moved incrementally through an X-Y plane through the tissue and the reference mirror. Brightness of the total of the combination of each pair of returned beams is computer analyzed to determine the extent of a reflecting layer at the depth of the focus of the reference beam. Then the reference beam is focused at an adjacent location at a different depth within the tissue. The process is repeated to define the extent of the reflecting layer of the adjacent tissue. By repeating the process at incremental adjacent tissue locations, the computer can construct a cross-sectional image of the entire mass of target tissue.

In the second method, the procedure can include (i) successively surveying layers along an axis substantially perpendicular to the emitter or (ii) successively surveying layers parallel to beams from the emitter. In either case, a cross-sectional image of the entire mass of target tissue may be constructed from the data received from the surveying procedures (i) and (ii).

In a typical Interferometer device, laser light is passed by way of flexible optical fibers to an interferometer head. The head is provided with a housing that encompasses essential optical components including a beam splitter that divides the laser light originating from a light source disposed outside the head. The light is split into a measuring beam and a reference beam. The measuring beam passes to the reflecting tissue that is to be measured. The reference beam passes outside the head to a fixed reference section such as a set mirror. The head can encompass a recombination device to superimpose the signals from the measuring beam and the reference beam. The superimposed signals form an optical interference signal that is passed by way of flexible optical fibers to a photoelectric detector device outside the interferometer head. The photoelectric detector device detects and evaluates the optical interference signal.

Interferometer devices are taught for example, in U.S. Pat. No. 5,303,030 to Abraham et al., U.S. Pat. No. 5,329,356 to Tabarelli et al., U.S. Pat. No. 5,349,440 to DeGroot and in U.S. Pat. No. 5,361,131 to Tekemori et al. The disclosures of these patents are incorporated herein by reference.

Figure 4:
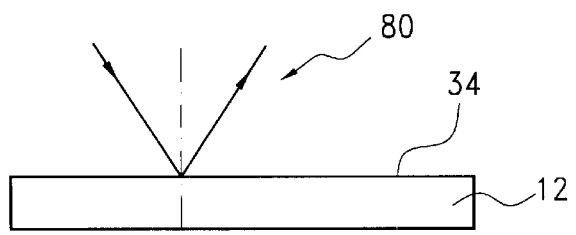
Figure 5:
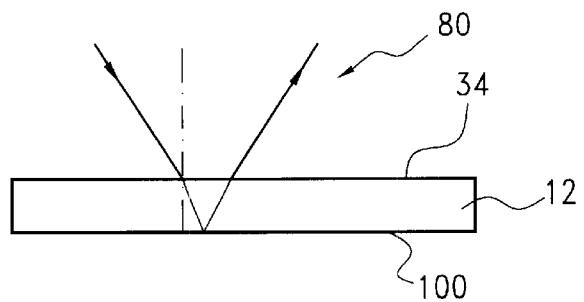

FIGS. 1 and 3 are schematic representations of preferred embodiments of the laser surgery device and method of treating biological tissue according to the present invention. FIGS. 2, 4 and 5 are schematic representations of thin film layers of biological tissue such as thin film layers of a cornea.

FIGS. 1 and 3 show laser surgery devices 14, 64 that utilize two-wavelength interferometry to determine the characteristics of a section of optical cornea tissue and to determine displacement characteristics of an incision that is cut into the cornea tissue during radial keratotomy.

In radial keratotomy, a number of precise incisions are made about the central optical zone of the cornea to relax the radius of curvature. The procedure can increase the focal length of the eye to correct or improve vision. Radial keratotomies are very delicate procedures requiring precision. The cornea is a transparent lens tissue covering the iris and pupil of the eye. Light is admitted into the eye through the cornea. The cornea is sensitive and delicate. The size and thickness of corneas vary from patient to patient. In performing a radial keratotomy, the length, width, depth and spacing of incisions must be precisely controlled in order to accomplish the desired object of improving vision without damaging the eye. The laser surgery devices 14, 64 and procedures illustrated in the Figures can control ablating of tissue to perform a radial keratotomy with high-intensity laser light by precise positioning of the laser beam and maximum absorption of the beam over a precise area and depth of incision.

According to the present invention, a sequence of detection can be used to evaluate the thickness and the boundary state of each layer of the cornea or other biological tissue. The cornea can be considered either a single layer or mutilayer thin film. The cornea can be evaluated as a mutilayer thin film to provide detailed information about cross-sectional planes of the cornea tissue or evaluated as a single layer thin film for applications requiring only gross information on the tissue structure. According to the invention, the information from the evaluation of the cornea has been found to be sufficient for processing to control the delicate ablation in a radial keratotomy and in other procedures for treating biological tissue by laser surgery.

FIG. 1 is a schematic representation of an interferometer 16 and optical system 18 that are emitter/receptor elements of laser surgery device 14. The interferometer 16 and optical system 18 of FIG. 1 can be utilized to create a spatialgram according to the apparatus and procedure of U.S. Pat. No. 5,227,861 to Nishizawa et al. The disclosure of this patent is incorporated herein by reference. Other references that describe three dimensional imaging systems that can be utilized in the present invention include U.S. Pat. No. 5,323,229 to May et al., U.S. Pat. No. 5,355,209 to Grosso and U.S. Pat. No. 5,365,340 to Ledger. The disclosures of these references are incorporated herein by reference.

As shown in FIG. 1, a light beam in a predetermined wave number region is emitted from light source 20. The light beam is transformed into a parallel light beam by an aspherical mirror 22. Interferometer 16 includes a beam splitter 24 for splitting the incident parallel light beam into two beams—a transmitted beam and a reflected beam. Fixed mirror 26 reflects the transmitted light beam and mobile mirror 28 reflects the reflected light beam back to the beam splitter 24 where the beams are synthesized to interfere with each other. Mobile mirror 28 is transferred at a constant speed in the direction shown by the arrow by driver 30. The transmitted light beam and the reflected light beam are synthesized while the optical path difference between the beams is continuously varied by transference of the mobile mirror 28. An interference light is synthesized on the beam splitter 24 and is modulated with time according to the constant speed of the mobile mirror 28. The interference beam synthesized at the beam splitter 24 is emitted out toward optical system 18.

At optical system 18, aspherical mirror 32 projects the interference light beam onto the surface 34 of cornea 12 at an incident angle. As shown schematically in FIG. 2, cornea 12 has surfaces 34 and 36. The interference light beam is designated incident light beam 38. Reflected light from front surface 34 is designated 40 and reflected light from back surface 36 is designated 42. Reflected light components 40 and 42 generate phase differences due to their respective different optical path lengths. The reflected beams 40 and 42 are converged through an aspherical mirror 44 onto the light-receiving surface of photodetector 46. The light receiving surface of photodetector 46 detects the reflected beams and measures an interferogram from the converged interference light beam. Processor 48 detects a signal from photodetector 46 that represents the interferogram. Processor 48 can be a computer. Processor 48 can include a Fourier transformer 50 as shown. Fourier transformer 52 transforms the interferogram, filters the resulting reflection spectrum and subjects the filtered reflection spectrum to reverse transforming to provide a spatialgram.

Processor 48 compares spatialgram data to data representing a standard of improved visual acuity to construct an ablating plan. Processor 48 can construct a virtual or real time display three dimensional image of the cornea film from the spatialgram and construct an ablating plan by comparing the constructed image to a representation of a standard of improved acuity. Processor 48 controls ablating laser 52 in accordance with the ablating plan.

Ablating laser device 52 includes laser generator 54 and laser beam irradiator 56 for applying a laser beam from the laser generator 54 as ablating beam 58 to an ablating target region 60 of the cornea 12 to form an incision. The ablating laser device 52 can include any device known in the art for conducting a radial keratotomy as for example devices disclosed in U.S. Pat. No. 4,648,400 to Schneider et al and U.S. Pat. No. 5,284,477 to Hanna et al. The device 52 includes an emitter for emitting a pulsed laser beam. The beam can comprise one lobe of elongated cross-section. A focussing means of irradiator 56 can focus the image of the lobe or lobes of the laser beam 58 onto the region 60 of the cornea 12 to be corrected. A displacement means 62 displaces ablating light beam 58 across the cornea 12 while focussing the lobe or lobes of beam 58 to complete correction of the cornea 12 as the summation of a plurality of elementary discrete ablations.

Ablating laser device 52 is responsive to the control of processor 48. The control step can comprise the processor 48 detecting a signal from the photodetector 46 and comparing the signal to a standard of improved acuity. The standard may be a shaped cornea that is has increased focal length and relaxed radius of curvature that is characterized by improved acuity compared to the target cornea 12 of eye 10. From the comparison, the processor 48 constructs an ablating plan for ablating incisions into the target cornea 12 or the processor 48 can construct a plan by accepting real time input, for example from a surgeon responding to a signal in the form of an image visually displayed on the screen of a computer. Processor 48 controls the ablating laser device 52 according to the ablating plan.

In FIGS. 3–5, components that are the same as components shown in FIGS. 1–2 are labeled with the same number. The method and device for treating biological tissue illustrated in FIG. 3 are other preferred embodiments of the invention. The method and device of FIG. 3 utilize precise three-dimensional imaging capability of low coherence interferometry to detect cornea tissue 12 to permit determination of the exact location and extent of a plurality of incisions necessary to correct cornea curvature. The three-dimensional imaging capability also permits precise control of ablating laser 52 in forming the incisions at the location and extent previously determined.

The laser surgical device 64 of FIG. 3, includes interferometer 66 that includes an optical source 68 that comprises a multimode laser diode that oscillates simultaneously at a number of discrete wavelengths to continuously provide a range of stable synthetic wavelengths. The spectral behavior of the multimode laser diode is predictable, free of mode hopping without appreciable change with time or temperature.

A lens element 70 focuses the output of laser diode 68 to an input coupler 72 of a collimating lens system 74. Polarizing beam splitter 76 provides reference beam 78 and measurement beam 80. Reference beam 78 and measurement beam 80 are orthogonally polarized one to another upon leaving the beam splitter 76 to improve the efficiency of the process. Each of the beams 78 and 80 passes through a quarter wavelength plate 82 and 84 for rotating the polarization of the beams. The plates 82 and 84 provide the respective beams 78 and 80 to focusing lens systems 86 and 88. The reference beam path includes a phase modulating element including a mirror 90 coupled to a piezoelectric actuator 92. The actuator 92 dithers the mirror 90 over a displacement and at a rate to provide a phase modulation to the multimode reference beam 78.

The focusing lens system 88 focuses the measurement beam 80 onto a measurement region on the surface of the X-Y tissue plane of cornea 12. Laser light reflecting from the mirror 90 and from the tissue plane of cornea 12 is provided, via the quarter wave plates 82 and 84 and beam splitter 76, to a polarizer 94 disposed in front of a focusing lens system 96. Polarizer 94 functions to collapse the differently polarized reference and measurement beams onto a common polarization. Lens system 96 provides for injecting the measurement and reference beams to photodetector 98. Processor 48 detects the output of photodetector 98 and determines an interferometric phase at two wavelengths. Processor 48 then computes an absolute distance to the surface of the cornea 12. By surveying the surface of cornea 12 by incrementally displacing the focus of measurement beam 80 along the surface, a plurality of absolute distances can be determined that permit processor 48 to construct a planar image of the surface.

FIG. 4 shows projecting a measurement beam 80 onto the cornea surface 12. FIG. 5 shows projecting measurement beam 80 through the cornea to focus on a back surface. The back surface can be surveyed by the procedure illustrated in FIG. 5 and reflected measurement beam signals can be filtered and adjusted to eliminate optical influences caused by passing the beam through the cornea structure to provide a planar image of the back surface. While FIG. 5 shows projecting the measurement beam 80 through the cornea, in another embodiment the back surface can be surveyed by irradiating the measurement beam directly onto the back surface by means of a remotely provided light source within the eye, for example a light source provided by a fiber optic.

From planar surveys of only the two surfaces or of multiple surfaces including tissue interface surfaces within the cornea 12, processor 48 provides a virtual or real time display three dimensional image of the cornea film and/or a file of data representing the film. An ablating plan is constructed by comparing the image and/or data to a representation of or data representing a standard of improved acuity as described above with reference to FIG. 1. Processor 48 controls ablating laser 52 in accordance with the ablating plan.

Ablating laser device 56 includes laser generator 58 and laser beam irradiator 60 for applying a laser beam from the laser generator 58 as ablating beam 62 to a target region 64 of the cornea 12 to form an incision. Ablating laser device 56 is controlled in accordance with the description above with reference to FIG. 1.

The present invention encompasses the use of low-coherence interferometry in several optical coherence tomography sequences to three dimensionally image a target cornea and to precisely incise the cornea with a laser. The detection of cornea tissue according FIGS. 3–5 can be accomplished by first determining a point on the surface of a tissue plane, such as for example an X-Y plane through the measurement region substantially perpendicular to the incident measurement beam. In a first sequence, the maximum brightness of combined reflected beams from equal distant points is determined to establish a reference maximum brightness representing synchronously arriving beams. The reference beam is then focused onto a reference region that may be a mirror placed at a known distance from the low coherence emitter 70. The measurement beam is focused onto corneal tissue at the precise same distance from the emitter as the reference region. The brightness of the reflected beams is measured. Any difference between the brightness representing synchronously arriving beams and the brightness when the measurement beam is focused onto corneal tissue is due to the disruption of wavelengths caused by the tissue. The difference in brightness is a characteristic of the tissue. The focus of both the reference beam and measurement beam is moved in tandem incrementally along the Z axis of the cornea tissue. A brightness measurement is made of the combined reflected beams at each incremental step. So long as the difference in brightness remains constant, the measurement beam is measuring a point along the Z axis of the cornea tissue. The extent of the tissue along the Z axis is determined by the extent of constant difference measurements. When the difference is no longer constant (the brightness is maximum or the brightness is different from the corneal tissue characteristic brightness), the measurement region is outside of the corneal tissue. By repeating measurements, an X-Z plane can be determined from a plurality of data points determined to be on the X-Z plane of the cornea tissue.

The reference beam is then focused onto a next reference region that may be a mirror placed at a known distance from the low coherence emitter at a different position along the Y axis of the tissue. The measurement beam again is focused onto the corneal tissue and a set of data points is determined defining a second X-Z plane displaced from the first plane. A series of cross-sectional images can be provided by repeating the X-Z plane determinations. The cross-sectional images define the cornea structure.

The reflecting reference region may be a focused point positioned outside of the eye that reflects the reference beam or the reference region can be provided by a reflecting surface such as a mirror-ended fiber inserted within or near the eye. The processor 48 accumulates electrical signals representing the reflected phase differences and constructs a virtual or real time display three dimensional image of the cornea film. The processor 48 then constructs the ablating plan by the comparing step to control laser surgery device 14.

Optical fibers can be used to position elements of the laser surgical device of the invention. For example in FIG. 2, an optical fiber may be used between the lens element 70 and the coupler 72. The use of an optical fiber can provide filtering to ensure that the source beam is spatially coherent and can permit positioning of the beam splitter 76 remotely from the laser diode.

In another procedure, an absolute distance to the target of biological tissue (for example, the distance between the ablating laser 52 and the surface of the cornea 12 can be determined by the procedure described with reference to FIGS. 3 and 4. The distance is determined by projecting a phase modulated measurement beam onto a target of biological tissue and projecting a reference beam onto a reference target; combining a reflected reference beam reflected from the reference target with a measurement beam reflected by the target of biological tissue; and evaluating a phase difference between the reference beam. The laser treating of the biological tissue can then be controlled with the distance information along with planar and/or three dimensional tissue information provided by the procedure described with reference to FIGS. 1 and 2 comprising projecting an interference light beam onto the target of biological tissue; detecting the interference light beam reflected by the target of biological tissue to provide an interferogram and evaluating the biological tissue on the basis of the interferogram.

The processor 48 can be a computer that determines the location and size of tumors or of cornea tissue and incisions and ablation using the information from the interferometer of FIG. 1 or FIG. 3 or a combination. Based on such information, the computer can determine the total power intensity, pulse duration and repetition rate and position of a light guide for irradiation laser 56. The computer can provide real time information graphic representation of structures such as a cornea along with information relating to the progress of ablation such as information on tissue destroyed or incised. The computer can construct an ablating plan by comparing information from the interferometer 16 or 66 to a standard of information representing characteristics of healthy tissue and tumor tissue in the case of tumor ablation or a standard of information representing a cornea with correct curvature as in radial keratotomy. The computer can be used to disable the laser irradiator 56 when the position of a light guide is determined to be capable of irradiation of health tissue in the case of tumor irradiation or capable of irradiation of tissue or a cornea that should be shielded from ablation in a procedure of radial keratotomy.

In another embodiment, ablation is concurrently controlled by detecting the extent of incision. Cornea ablation by ablating beam 58 is controlled by detecting the extent of incision with the interference beam during ablation and simultaneously controlling ablating beam 58. The power intensity, pulse duration and repetition rate and focus of the beam 58 can be concurrently adjusted according to a comparison with the incisions previously determined by the surgical model of the ablating plan. The cornea ablation can be controlled by using the ablating beam 58 by intermittently emitting a measuring pulse that determines the extent of incision and compares the extent to the surgical model. The power intensity, pulse duration and repetition rate and focus of the beam 58 be controlled from the comparison.

Ablation can be controlled by both setting the ablation according to the plan and adjusting the ablation during laser surgery by comparing the ablation to the plan and adjusting the ablation according to the comparing step. The ablation can be adjusted during laser surgery by detecting the ablation by detecting an incision with the interference light of the optical system 18 or by detecting the incision by intermittent detecting pulses of ablating beam 58 or by detecting the incision by a combination of both the interference light and intermittent detecting pulses of the ablating beam 58. An example of the last mentioned embodiment comprises detecting the location of the incision or point of incision on a plane of the tissue of cornea 12 with the interference light and detecting the depth of incision from the surface of the cornea with the intermittent pulse of ablating beam 58 to provide a three dimensional image of the cornea 12 with incision that can be compared to the ablation plan. The location and intensity of the ablating beam 58 of ablating laser 52 can be maintained in accordance with the plan or instantaneously adjusted to correct any deviation from the plan.

Other modifications of the present invention will occur to those skilled in the art subsequent to a review of the present application. For example, the device of FIG. 1 can be modified to determine an image of a cornea or other optically transmissive tissue by sequentially determining thickness by coherence shifting interferometry wherein the system utilizes an optical energy source for generating a source beam. The source beam is divided into two beams by reflecting one portion of the beam off of a reflective surface such as the front surface of a cornea having an unknown thickness. A second portion of the beam is transmitted through the sample and reflected off a refractive interface in the sample such as the back surface of the cornea. The two reflected beams are combined into a composite beam. The composite beam is directed to a Mach-Sehnder type interferometer, where a portion of the combined beam traverses a fixed optical path length and another portion traverses a variable optical path length. The variable optical path length is adjusted to realign portions of the two beams and cause interference. The amount of adjustment provides a measure of the unknown thickness that can be analyzed by a processor for control of an ablating laser.

These modifications and equivalents thereof are intended to be included within the scope of this invention.

What is claimed is:

1. A method of treating biological tissue by laser surgery, comprising detecting a limit or location of surface or mass of biological tissue by a process of interferometry and controlling the laser treating of said biological tissue according to the detected limit or location of surface or mass.

2. The method of claim 1, comprising controlling a method of radial keratotomy.

3. The method of claim 1, comprising detecting said extent of said surface or mass of biological tissue by a process of optical coherence tomography.

4. The method of claim 1, wherein said controlling step comprises controlling a laser beam irradiator according to an ablating plan constructed according to said detecting step.

5. The method of claim 4, wherein said controlling step comprises controlling a laser beam irradiator according to an ablating plan constructed according to said detecting step and (i) by detecting ablating incision by said process of interferometry, (ii) by detecting ablating incision by an intermittent pulse from said laser beam irradiator or (iii) by a combination of detecting ablating incision by said process of interferometry and by an intermittent pulse from said beam irradiator.

6. The method of claim 1 for ablating biological tissue, comprising:

(A) detecting the limits of a surface plane of biological tissue by scanning the tissue with a phase modulated measurement beam; and (B) ablating the limits of the surface plane of tissue according to said detecting step.

7. The method of claim 6 comprising successively detecting limits of layers of tissue while successively ablating the limits of said layers of tissue.

8. The method of claim 1, comprising:

(A) projecting an interference light beam onto a multilayer target of biological tissue;

(B) detecting the interference light beam reflected by said multilayer target to provide an interferogram;

(C) evaluating said multilayer target on the basis of said interferogram; and (D) controlling the laser treating of said biological tissue according to said evaluating step.

9. The method of claim 8, comprising:

(A) synthesizing two light beams in a predetermined wave number region while continuously varying optical path differences thereof to produce an interference light beam and projecting said interference light beam onto a multilayer target of biological tissue;

(B) detecting the interference light beam reflected by said multilayer target to provide an interferogram;

(C) evaluating said multilayer target by performing Fourier transform on said interferogram to provide a reflection spectrum filtered to provide a spatialgram; and (D) controlling the laser treating of said biological tissue according to the spatialgram provided in said evaluating step.

10. The method of claim 9, comprising conducting a sequence of steps (A), (B) and (C) to provide the thickness and the boundary state of a layer of said biological tissue and controlling said laser treating of biological tissue according to thickness and boundary state of the layer.

11. The method of claim 10, comprising constructing a three dimensional image of said biological tissue according to said sequence of steps and comparing said three dimensional image of said tissue to a standard to provide an ablating plan and controlling the laser treating of said biological tissue according to said ablating plan.

12. The method of claim 1, comprising:

(A) projecting a phase modulated measurement beam onto a target of biological tissue and projecting a reference beam onto a reference target;

(B) combining a reflected reference beam reflected from said reference target with a reflected measurement beam reflected by the target of biological tissue;

(C) evaluating a phase difference between the reflected reference beam and the reflected measurement beam; and (D) controlling the laser treating of said biological tissue according to said evaluating step.

13. The method of claim 12, comprising repeating said steps (A), (B) and (C) to provide a set of repetitively detected phase differences that are evaluated by a comparison with a representation of a standard of biological tissue.

14. The method of claim 13, further comprising constructing an image of said biological tissue from said set of repetitively detected phase differences and comparing said image to a representation of a standard to construct an ablating plan for said laser treating step (D).

15. The method of claim 14, comprising focusing a treatment laser beam on the said biological tissue according to said evaluating step to achieve selective surgery of said biological tissue according to repetitively detected phase differences.

16. The method of claim 12, wherein step (A) comprises (i) projecting said measurement beam to successively survey layers along an axis substantially perpendicular to the projection of said beam or (ii) projecting said measurement beam to successively survey layers substantially parallel to the projection of said beam and constructing a cross-sectional image of the entire mass of target tissue from evaluating the phase difference step (C).

17. The method of claim 16, comprising (a) surveying a plane of said target tissue by successively projecting said measurement beam onto a plane of said target region having X-Y axes to define said plane, (b) successively surveying a next plane incrementally displaced along a Z axis perpendicular to said X-Y axes, and (c) repeating step (b) to provide a three dimensional image for comparing to a standard to construct an ablating plan.

18. The method of claim 12, comprising determining an absolute distance to the target of biological tissue according to steps (A), (B), and (C); and (i) projecting an interference light beam onto the target of biological tissue; (ii) detecting the interference light beam reflected by said target of biological tissue to provide an interferogram; and (D) controlling the laser treating of the biological tissue according to said absolute distance and said interferogram.

19. A laser surgery device, comprising:
 laser beam irradiator for applying a laser beam to a target region of biological tissue;
 interferometer for projecting a light beam onto said target region of biological tissue, including a detector for receiving a reflected interference beam from said target region, detecting a phase difference of said interference beam and providing an electrical signal according to said phase difference; and
 a controller responsive to said electrical signal for controlling an output of applied laser beam from said laser beam irradiator.

20. The laser surgery device of claim 19, wherein said controller comprises a processor that compares said electrical signal to a standard, constructs an ablating plan according to the comparison and controls the output of applied laser beam from the laser beam irradiator according to the ablating plan.

21. The laser surgery device of claim 19, wherein said controller comprises a processor that compares said electrical signal to a standard and determines factors of total power intensity, pulse duration, repetition rate or position of a light guide for said laser beam irradiator and controls the output of applied laser beam from the laser beam irradiator according to the determined factors.

22. The laser surgery device of claim 19, wherein said interferometer comprises:
 (A) an optical source comprising a multimode laser diode that provides a light beam having a range of stable wavelengths;
 (B) a lens element that focuses the light beam onto a beam splitter that splits said light beam to provide a reference beam and a measurement beam;
 (C) a focusing system for receiving the reference beam and focusing the reference beam onto a phase modulating element that provides a phase modulation to the reference beam;
 (D) a focusing system for receiving the measurement beam and focusing the measurement beam onto a measurement region that reflects said measurement beam;
 (E) polarizer that receives a reflected reference beam from the phase modulating element and a reflected measurement beam from said measurement region and collapses the differently polarized reference and measurement beams onto a common polarization; and
 (F) a lens system that injects the reference and measurement beams to the detector.

23. The laser surgery device of claim 19, wherein said interferometer comprises:
 (A) an optical source for emitting a light beam in a predetermined wave number region;
 (B) beam splitter for transforming the emitted light beam into a transmitted beam and a reflected beam;
 (C) mirrors for reflecting said transmitted and reflected beams in different paths said beam splitter for synthesizing an interference beam from said reflected beams; and
 (B) an emitter that emits said interference beam onto said target region of biological tissue.

24. The laser surgery device of claim 23, including Fourier transformer for performing Fourier transform to provide a spatialgram from said phase difference that is converted into said electrical signal.

25. The laser surgery device of claim 23, including Fourier transformer for performing Fourier transform to provide a reflection spectrum, filtering means for filtering the reflection spectrum, complex power reverse Fourier transformer for performing power reverse Fourier transform on the reflection spectrum filtered to provide a spatialgram and a processor for evaluating the target region on the basis of the electrical signal converted from the spatialgram and said laser beam irradiator is responsive to the evaluator.

* * * * *